(12) United States Patent
Boschetti et al.

(10) Patent No.: US 7,815,783 B2
(45) Date of Patent: Oct. 19, 2010

(54) MULTI-COMPARTMENT FILTER AND METHOD OF FILTERING USING SAME

(75) Inventors: Egisto Boschetti, Croissy sur Seine (FR); Lee O. Lomas, Pleasanton, CA (US); Pierre Girot, Paris (FR)

(73) Assignee: Bio-Rad Laboratories, Inc., Hercules, CA (US)

( * ) Notice: Subject to any disclaimer, the term of this patent is extended or adjusted under 35 U.S.C. 154(b) by 1161 days.

(21) Appl. No.: 11/073,999

(22) Filed: Mar. 8, 2005

(65) Prior Publication Data

US 2005/0205427 A1      Sep. 22, 2005

Related U.S. Application Data

(60) Provisional application No. 60/553,605, filed on Mar. 17, 2004, provisional application No. 60/575,413, filed on Jun. 1, 2004.

(51) Int. Cl.
    *G01N 27/453*  (2006.01)
    *B01D 57/02*  (2006.01)
(52) U.S. Cl. .................. 204/644; 204/548; 204/610
(58) Field of Classification Search .............. 204/459, 204/548, 610, 644
    See application file for complete search history.

(56) References Cited

U.S. PATENT DOCUMENTS

| | | | |
|---|---|---|---|
| 4,243,507 A | 1/1981 | Martin et al. | |
| 4,362,612 A | 12/1982 | Bier | |
| 4,963,236 A | 10/1990 | Rodkey et al. | |
| 4,971,670 A | 11/1990 | Faupel et al. | |
| 5,087,338 A | 2/1992 | Perry et al. | |
| 5,173,164 A | 12/1992 | Egen et al. | |
| 5,328,578 A * | 7/1994 | Gordon ....................... | 204/452 |
| 5,393,430 A | 2/1995 | Girot et al. | |
| 5,445,732 A | 8/1995 | Girot et al. | |
| 5,470,463 A | 11/1995 | Girot et al. | |
| 5,834,272 A | 11/1998 | Righetti | |
| 6,013,165 A * | 1/2000 | Wiktorowicz et al. ....... | 204/456 |

(Continued)

FOREIGN PATENT DOCUMENTS

WO    WO 03/101591 A1 * 12/2003

OTHER PUBLICATIONS

Cretich et al, Electrophoresis 2003, 24, pp. 577-581.*

(Continued)

*Primary Examiner*—Kaj K Olsen
(74) *Attorney, Agent, or Firm*—Morgan, Lewis & Bockius, LLP

(57) ABSTRACT

Each embodiment includes a central sample reservoir and a plurality of satellite reservoirs. In a first embodiment, a first electrode in electrical contact with the central reservoir is charged and second electrodes in electrical contact with the satellite reservoirs are sequentially charged, thereby pI filtering molecules in the central reservoir into the satellite reservoirs. In a second embodiment, the central reservoir is configured to rotate so that molecules in a sample in the central reservoir are centrifugally pI-filtered into the satellite reservoirs. In a third embodiment, first and second electrodes proximate opposite first and second satellite reservoirs, respectively, are charged. Some molecules in a sample are pI filtered into the first and second satellite reservoirs. Third and fourth electrodes proximate opposite third and fourth satellite reservoirs, respectively, are then charged. Some molecules in a sample are pI filtered into the third and fourth satellite reservoirs.

22 Claims, 4 Drawing Sheets

U.S. PATENT DOCUMENTS

| | | | |
|---|---|---|---|
| 6,613,234 | B2 | 9/2003 | Voute et al. |
| 7,166,202 | B2 * | 1/2007 | Bukshpan et al. ........... 204/459 |
| 2002/0005383 | A1 | 1/2002 | Voute et al. |
| 2002/0043465 | A1 * | 4/2002 | Vigh et al. ................. 204/548 |
| 2006/0049050 | A1 * | 3/2006 | Faupel et al. ............... 204/450 |

OTHER PUBLICATIONS

P. G. Righetti, et al., "Preparative Protein Purification in a Multi-Compartment Electrolyser with Immobiline Membranes," 475 J. Chromatography 293-309 (1989).

P. G. Righetti, et al., "Preparative Purification of Human Monoclonal Antibody Isoforms in a Multi-Compartment Electrolyser with Immobiline Membranes," 500 J. Chromatography 681-696 (1990).

P. G. Righetti, et al., "Preparative Electrophoresis with and without Immobilized pH Gradients," 5 Advances in Electrophoresis 159-200 (1992).

Ribeiro, J,M. and Sillero, A., "An algorithm for the computer calculation of the coefficients of a polynomial that allows determination of isoelectric points of proteins and other macromolecules", Computers in Biology & Medicine 20(4):235-42 (1990).

Ribeiro, J.M. and Sillero, A., "A program to calculate the isoelectric point of macromolecules" Computers in Biology & Medicine 21(3):131-41 (1991).

Sillero, A. and Ribeiro, J.M., "Isoelectric points of proteins: theoretical determination" Analytical Biochemistry 179(2):319-25 (1989).

* cited by examiner

MULTI-COMPARTMENT FILTER AND METHOD OF FILTERING USING SAME

CROSS-REFERENCE TO RELATED APPLICATIONS

This application claims priority to U.S. Provisional Patent Application Nos. 60/553,605 and 60/575,413, which were filed on Mar. 17, 2004, and Jun. 1, 2004, respectively.

BACKGROUND OF THE INVENTION

The need to isolate particular molecules, e.g., proteins, has long been known. Moreover, various protocols exist by which molecules may be isolated. For example, in gel electrophoresis proteins are placed in the middle of a buffered gel (e.g., polyacrylamide gel) between oppositely charged electrodes. When the electrodes are charged, each of the protein molecules travels toward one of the electrodes, according to their net charge at the pH of the buffered polyacrylamide gel. The speed at which the protein molecules move through the gel toward the electrodes is largely dependent on the size of the molecule, i.e., smaller molecules move faster through the gel matrix. As a result in the differences in speed, types of protein molecules can be separated and then isolated.

A variant to gel electrophoresis is isoelectric focusing, which exploits the fact that the net charge of a protein depends on the environmental pH. Most generally, at acidic pH, proteins are globally positively charged while in alkaline pH they are negatively charged. The pH at which the protein has no net charge is called the isoelectric point ("pI"). Isoelectric focusing is an electrophoresis technique in which proteins move under an electric field through a pH gradient. All proteins migrate towards the cathode or the anode until they encounter a pH identical to their isoelectric point. At this point the protein loses its charge and stops moving. Proteins of different isoelectric points stop at different levels and are thus separated. Accordingly, similarly sized molecules, which may move at similar speeds, can be separated after coming to rest at different pH points, as a result of having different pI values. In addition, there are situations in which migration by the size in a given buffered gel and migration by the isoelectric point are crossed for an enhanced separation of protein species from very complex mixtures; the technique used in this situation is called bidimensional electrophoresis. Unfortunately, migration of proteins within an electrophoresis gel network according to these techniques is a very slow process and is generally unacceptable for preparative purposes.

In response, various additional protocols have been developed which have attempted to increase the rate of separation, while preserving the accuracy by which it is performed. There are many types of devices comprising two or more subcompartments that are separated from each other by septa, e.g., monofilament screens, membranes, gels, filters, fritted discs, and the like (collectively, "membranes"). Generally, these devices are assembled from a plurality of essentially parallel frames or spacers, separated from each other by one or more membranes.

Multi-compartment electrolizers with isoelectric membranes were introduced for processing large volumes and amounts of proteins to homogeneity. For example, see P. G. Righetti, et al., "Preparative Protein Purification in a Multi-Compartment Electrolyser with Immobiline Membranes," 475 J. CHROMATOGRAPHY 293-309 (1989); P. G. Righetti, et al., "Preparative Purification of Human Monoclonal Antibody Isoforms in a Multi-Compartment Electrolyser with Immobiline Membranes," 500 J. CHROMATOGRAPHY 681-696 (1990); P. G. Righetti, et al., "Preparative Electrophoresis with and without Immobilized pH Gradients," 5 ADVANCES IN ELECTROPHORESIS 159-200 (1992). Based on isoelectric focus, this purification concept progresses under recycling conditions. The protein macro-ions are kept in a reservoir and are continuously passed through an electric field across a multicompartment electrolyzer equipped with zwitterionic membranes.

In this system the protein is always kept in a liquid vein, also called a "channel." Consequently, the protein is not lost by adsorption onto surfaces, as typically occurs in chromatographic procedures. Rather, the protein is trapped in a chamber that is delimited by two membranes which have pI values encompassing the pI value of the protein to be separated. Thus, by a continuous titration process, all other impurities, either non-isoelectric or having different pI values, are forced to leave the chamber. In the end, the isoelectric/isoionic protein of interest will ultimately be present, as the sole species, in the chamber. It should be recognized, however, that the isoelectric and isoionic points of a protein can differ to some extent in the presence of counterions.

U.S. Pat. No. 4,971,670 describes this process. Isoelectric membranes also are addressed in U.S. Pat. No. 4,243,507. U.S. Pat. No. 5,834,272 describes an immobilization of enzymes that keeps them in solution and, hence, under conditions of homogeneous catalysis.

In U.S. Pat. No. 4,362,612, adjoining compartments are functionally designed to adjust to different pH values electrophoretically, thereby separating dissolved proteins according to their isoelectric points. Similar multiple subcompartments devices are described in U.S. Pat. Nos. 4,971,670, 5,173,164, 4,963,236, and 5,087,338. Each of these patents discloses a device comprised of a series of parallel spacers, separated from each other by membranes, that provides an essentially parallel array of subcompartments. Similarly, Amersham Pharmacia created an IsoPrime filter using a plurality of pI-selective membranes arranged in series. In this device the membranes are arranged in ascending or descending pI-selectivity. As a solution passes through the membranes, molecules having pI values between two consecutive membranes are trapped between the membranes. However, this process takes on the order of hours to complete. Invitrogen, Inc. invented a device, the ZOOM IEF Fractioner, which is substantially similar to the IsoPrime device, but which enables the membranes to be individually replaced. However, like the IsoPrime, the ZOOM IEF Fractioner process takes on the order of hours to complete.

What is needed, therefore, is an apparatus and a methodology that address at least one if not more of the deficiencies that afflict conventional practice, as previously described. More particularly, the need exists for an approach for separating molecules, such as proteins, quickly and accurately accordingly to pI values.

SUMMARY OF THE INVENTION

An embodiment of the present invention addresses a filter apparatus that includes, among other possible things: (a) a central reservoir configured to contain a sample; (b) a plurality of satellite reservoirs; (c) a plurality of portals, each portal joining a satellite reservoir in liquid communication with the central reservoir; (d) a plurality of filtration devices, the devices differing from each other in pI-selectivity, wherein each device is positioned in a portal; (e) a first electrode configured to be in electrical contact with a sample in the central reservoir, and (f) at least one second electrode configured to be in electrical contact with fluid in at least one of the satellite reservoirs.

Another embodiment of the present invention addresses a filter apparatus that includes, among other possible things: (a) a central reservoir configured to contain a sample; (b) at least a first and a second satellite reservoir in fluid communication with the central reservoir; (c) at least a first and a second portal, each portal joining the at least first and second satellite reservoirs, respectively, with the central reservoir; (d) at least a first and a second filtration device, differing from each other in pI-selectivity, wherein each of the first and second filtration devices are positioned in the at least first and second portals, respectively; (e) a first electrode configured to be in electrical contact with a sample in the central reservoir, and (f) at least one second electrode configured to be in electrical contact with fluid in at least one of the satellite reservoirs, wherein a primary of said second electrodes is configured to be in electrical contact with fluid in the first satellite reservoir.

In a further embodiment of this filter apparatus, the filter apparatus may also include: (g) a secondary second electrode configured to be in electrical contact with fluid in a second satellite reservoir; and (h) a switching apparatus configured to: (i) charge the first electrode and the primary second electrode; and (ii) subsequently de-charge the primary second electrode and charge a secondary second electrode.

In another further embodiment of this filter apparatus, the filtration devices associated with the satellite reservoirs may be zwitterionic barriers.

In another further embodiment of this filter apparatus, the filtration devices associated with the satellite reservoirs may comprise a sequence of barriers. Further, at least one of the barriers may be a zwitterionic barrier. In another further embodiment of this filter apparatus, at least one of the barriers in the sequence of barriers may be a membrane or may be particulate matter comprising a selective ligand. Further, the membrane or particulate matter may be positioned between the zwitterionic barrier and the satellite reservoir.

In another further embodiment of this filter apparatus, the filtration devices associated with the satellite reservoirs may comprise a sequence of barriers. Further, at least one of the barriers may be a zwitterionic packed particulate material. In another further embodiment of this filter apparatus, the particulate material may have an irregular or spherical shape. Additionally or alternatively, the particulate material may be formed of a polymeric material or a composite material.

In another further embodiment of this filter apparatus, the filter apparatus may also include: at least one cut-off membrane positioned between at least one second electrode and satellite reservoir. Further, the cut-off membrane may be impermeable to molecules greater than 500 Daltons.

In another further embodiment of this filter apparatus, the filter apparatus may also include: a power source comprising two oppositely charged poles electrically connected to the first electrode and at least one of the second electrodes, respectively.

In another further embodiment of this filter apparatus, the first electrode may be separated from each of the second electrodes by a distance of no more than about 1 cm, no more than about 5 cm, no more than about 10 cm, no more than about 15 cm, no more than about 20 cm, no more than about 30 cm, no more than about 35 cm, no more than about 40 cm, no more than about 45 cm, or no more than about 50 cm.

In another further embodiment of this filter apparatus, the filter apparatus may also include: a sample, which is provided in the central reservoir, that comprises amphoteric molecules. In another further embodiment of this filter apparatus, the amphoteric molecules may comprise proteins.

In another further embodiment of this filter apparatus, the filtration devices may have pI-selectivity values that differ from each other in increments selected from the group consisting of about 0.001 pH unit, about 0.01 pH unit, about 0.1 pH unit, and about 1.0 pH unit.

In another further embodiment of this filter apparatus, the central reservoir may be configured to rotate or may be configured to stir a sample therein.

In another further embodiment of this filter apparatus, the first electrode may be configured to be charged. Further, each of the second electrodes may be configured to be charged oppositely than the first electrode. Further, when the first electrode and the primary second electrode are charged, molecules in a sample positioned in the central reservoir having pI values greater than or less than the pI-selectivity of the first filtration device may move into the first satellite reservoir.

In another further embodiment of this filter apparatus, the filtration devices may be membranes formed of a polyacrylamide gel to which an acrylamido buffer is covalently linked.

In another further embodiment of this filter apparatus, each of the filtration devices may comprise an isoelectric bead bed or substantially porous particle body.

Another embodiment of the present invention addresses a method of filtering. This method includes, among other possible steps: (a) providing a sample in a central reservoir, wherein the central reservoir is in fluid communication with a plurality of satellite reservoirs comprising at least a first, a second, and a third satellite reservoir, wherein a plurality of portals join at least some of the satellite reservoirs and the central reservoir and comprise at least a first, a second, and a third portal, wherein a plurality of filtration devices are positioned in at least some of the portals and comprise at least a first, a second, and a third filtration device, wherein at least some of the filtration devices differ from each other in pI-selectivity, and wherein the first, second, and third filtration devices are positioned in the first, second, and third portals, respectively; (b) charging a first electrode in electrical contact with the sample in the central reservoir; (c) charging a primary second electrode in electrical contact with fluid in the first satellite reservoir, wherein the primary second electrode has an opposite charge than the first electrode; (d) moving molecules in the sample having pI values greater than, or less than, a pI-selectivity of the first filtration device into the first satellite reservoir; (e) eliminating the charge of the primary second electrode; (f) charging a secondary second electrode in electrical contact with fluid in the second satellite reservoir, wherein the secondary second electrode has an opposite charge than the first electrode; and (g) moving molecules in the sample having pI values between the pI-selectivities of the first and second filtration devices into the second satellite reservoir.

In a further embodiment of this method, the method may also include the steps of: (h) eliminating the charge of the secondary second electrode; (i) charging a tertiary second electrode in electrical contact with fluid in the third satellite reservoir, wherein the tertiary second electrode has an opposite charge than the first electrode; and j) moving molecules in the sample having pI values between the pI-selectivities of the second and third filtration devices into the third satellite reservoir.

In another further embodiment of this method, the method may also include the step of: (h) rotating the sample.

In another further embodiment of this method, at least one of the filtration devices may be a zwitterionic barrier.

In another further embodiment of this method, at least one of the filtration devices may comprise a zwitterionic packed particular matter.

In another further embodiment of this method, the particulate material may have an irregular or spherical shape. In another further embodiment of this method, the particulate material may be formed of a polymeric material or a composite material.

In another further embodiment of this method, at least one of the filtration devices may be formed of a polyacrylamide gel to which an acrylamido buffer is covalently linked.

In another further embodiment of this method, at least one of the filtration devices may comprise an isoelectric bead bed or substantially porous particle body.

Another embodiment of the present invention a filter apparatus that includes, among other possible things: (a) a central reservoir configured to contain a sample; (b) a plurality of satellite reservoirs in fluid communication with the central reservoir; (c) a plurality of portals joining at least some of the satellite reservoirs and the central reservoir and comprising at least a first and a second portal; (d) a plurality of filtration devices comprising at least a first and a second filtration device, wherein at least some of the filtration devices differ from each other in molecular affinity, and wherein the first and second filtration devices are positioned in the first and second portals, respectively. The apparatus is configured to rotate about an axis, which is orthogonal to a plane formed by the central and satellite reservoirs.

In a further embodiment of this filter apparatus, the molecular affinity may be pI-selectivity. In another further embodiment of this method, the plurality of satellite reservoirs may comprise at least a first and a second satellite reservoir. When the apparatus rotates, (i) molecules in a sample in the central reservoir having pI values greater than or less than the pI-selectivity of the first filtration device may move into the first satellite reservoir and (ii) molecules in the sample having pI values between the pI-selectivities of the first and second filtration devices may move into the second satellite reservoir. Additionally or alternatively, in another further embodiment of this method, the filtration devices may have pI-selectivity values that differ from each other in increments selected from the group consisting of about 0.001 pH unit, about 0.01 pH unit, about 0.1 pH unit, and about 1.0 pH unit.

In another further embodiment of this method, at least one of the filtration devices may comprise an isoelectric bead bed or substantially porous particle body.

In another further embodiment of this method, the sample may comprise amphoteric molecules. In another further embodiment of this method, the amphoteric molecules may comprise proteins.

In another further embodiment of this method, each of the satellite reservoirs may be in fluid communication with a respective plurality of regional reservoirs. Further, regional filtration devices may be positioned between each of the regional reservoirs and the satellite reservoir associated therewith. Moreover, each of the regional filtration devices associated with each of the satellite reservoirs may have a different pI-selectivity.

Another embodiment of the present invention addresses a method of filtering. This method includes, among other possible steps: (a) providing a sample in a central reservoir, wherein the central reservoir is in fluid communication with a plurality of satellite reservoirs comprising at least a first, a second, and a third satellite reservoir, wherein a plurality of portals join at least some of the satellite reservoirs and the central reservoir and comprise at least a first, a second, and a third portal, wherein a plurality of filtration devices are positioned in at least some of the portals and comprise at least a first, a second, and a third filtration device, wherein at least some of the filtration devices differ from each other in pI-selectivity, and wherein the first, second, and third filtration devices are positioned in the first, second, and third portals, respectively; (b) rotating the sample; (c) moving molecules in the sample having pI values greater than, or less than, a pI-selectivity of the first filtration device into the first satellite reservoir; and (d) moving molecules in the sample having pI values between the pI-selectivities of the first and second filtration devices into the second satellite reservoir.

In a further embodiment of this method, the method may also include the step of: (e) moving molecules in the sample having pI values between the pI-selectivities of the second and third filtration devices into the third satellite reservoir. In another further embodiment of this method, the method may also include the step of: (f) moving molecules into the remaining satellite reservoirs. Each of the remaining satellite reservoirs may receive a different set of molecules determined by the molecules' pI values.

In another further embodiment of this method, at least one of the filtration devices may comprise an isoelectric bead bed or substantially porous particle body.

In another further embodiment of this method, the filtration devices may have pI-selectivity values that differ from each other in increments selected from the group consisting of about 0.001 pH unit, about 0.01 pH unit, about 0.1 pH unit, and about 1.0 pH unit.

In another further embodiment of this method, the step of (b) rotating the sample may comprise: rotating the central reservoir and the satellite reservoirs.

In another further embodiment of this method, each of the satellite reservoirs may be in fluid communication with a respective plurality of regional reservoirs. Further, pI-selective regional filtration devices may be positioned between each of the satellite reservoirs and the regional reservoirs associated therewith. Moreover, the method may also include the steps of: (e) moving molecules in the first satellite reservoirs having pI values greater than, or less than, a pI-selectivity of the filtration device associated with a primary of the plurality of regional reservoirs associated with the first satellite reservoir into the primary regional reservoir; and (f) moving molecules in the first satellite reservoir having pI values between the pI-selectivities of the filtration devices associated with the primary and a secondary of the plurality of regional reservoirs associated with the first satellite reservoir into the secondary regional reservoir.

Another embodiment of the present invention addresses a kit apparatus that includes, among other possible things: (a) a central reservoir configured to contain a sample; (b) at least a first and a second satellite reservoir in fluid communication with the central reservoir; (c) at least a first and a second portal joining at least the first and second satellite reservoirs with the central reservoir; (d) at least a first and a second filtration device, differing from each other in pI-selectivity, wherein the first and second filtration devices are configured to be positioned in the first and second portals, respectively; (e) a first electrode configured to be positioned in electrical contact with a sample in the central reservoir, and (f) at least one second electrode configured to be positioned in electrical contact with fluid in at least one of the satellite reservoirs.

In a further embodiment of this kit apparatus, the kit may also include: a switching apparatus configured to: (i) charge the first electrode and a primary second electrode; and (ii) subsequently de-charge the primary second electrode and charge a secondary second electrode.

In another further embodiment of this kit apparatus, the filtration devices may be zwitterionic barriers.

In another further embodiment of this kit apparatus, the filtration devices may comprise a sequence of barriers. Further, at least one of the barriers may be a zwitterionic barrier.

In another further embodiment of this kit apparatus, at least one of the barriers in the sequence of barriers may be a membrane or may be particulate matter comprising a selective ligand. Further, the membrane or particulate matter may be positioned between the zwitterionic barrier and the satellite reservoir.

In another further embodiment of this kit apparatus, the filtration devices may comprise a sequence of barriers. Further, at least one of the barriers may be a zwitterionic packed particulate material. In another further embodiment of this kit apparatus, the particulate material may have an irregular or spherical shape. Additionally or alternatively, the particulate material may be formed of a polymeric material or a composite material.

In another further embodiment of this kit apparatus, the kit may also include: at least one cut-off membrane configured to be positioned between at least one second electrode and satellite reservoir. Further, the cut-off membrane may be impermeable to molecules greater than 500 Daltons.

In another further embodiment of this kit apparatus, the kit may also include: a power source comprising two oppositely charged poles electrically configured to be connected to the first electrode and at least one of the second electrodes, respectively.

In another further embodiment of this kit apparatus, the filtration devices may have pI-selectivity values that differ from each other in increments selected from the group consisting of about 0.001 pH unit, about 0.01 pH unit, about 0.1 pH unit, and about 1.0 pH unit.

In another further embodiment of this kit apparatus, the central reservoir may be configured to rotate or may be configured to stir a sample therein.

In another further embodiment of this kit apparatus, the filtration devices may be membranes formed of a polyacrylamide gel to which an acrylamido buffer is covalently linked.

In another further embodiment of this kit apparatus, each of the filtration devices may comprise an isoelectric bead bed or substantially porous particle body.

Another embodiment of the present invention addresses a filter apparatus that includes, among other possible things: (a) a central reservoir configured to contain a sample; (b) at least a first, a second, a third, and a fourth satellite reservoir in fluid communication with the central reservoir; (c) at least a first, a second, a third, and a fourth portal joining at least the first, second, third and fourth satellite reservoirs with the central reservoir; (d) at least a first, a second, a third, and a fourth filtration device, differing from each other in pI-selectivity, wherein the first, second, third, and fourth filtration devices are positioned in the first, second, third, and fourth portals, respectively, wherein the first filtration device is either a highest-pI-selective or a lowest-pI-selective filtration device and the second filtration device is the other of the highest-pI-selective or the lowest-pI-selective filtration device, and wherein the third filtration is either a higher-pI-selective or a lower-pI-selective filtration device and the fourth filtration device is the other of the higher-pI-selective or the lower-pI-selective filtration device; and (e) at least a first electrode configured to be in electrical contact with the first satellite reservoir, a second electrode configured to be in electrical contact with the second satellite reservoir, a third electrode configured to be in electrical contact with the third satellite reservoir, and a fourth electrode configured to be in electrical contact with the fourth satellite reservoir, wherein the first and the second electrodes are oppositely charged, wherein the first and the second satellite reservoirs are oppositely positioned across the central reservoir, wherein the third and the fourth electrodes are oppositely charged, and wherein the third and the fourth satellite reservoirs are oppositely positioned across the central reservoir. In a first separation step, the first and second electrodes are configured to be charged so that molecules move through the highest-pI-selective and lowest-pI-selective filtration devices and into the first and second satellite reservoirs. After the first separation step, the first and second electrodes are configured to be de-charged and the third and fourth electrodes are configured to be charged so that molecules move through the higher-pI-selective and lower-pI-selective filtration devices and into the third and fourth satellite reservoirs, thereby leaving molecules having pI values between the pI-selectivities of the higher-pI-selective and lower-pI-selective filtration devices in the central reservoir.

In a further embodiment of this filter apparatus, the filter apparatus may also include: a switching apparatus configured to charge and de-charge the electrodes.

In another further embodiment of this filter apparatus, the filtration devices associated with the satellite reservoirs may be zwitterionic barriers.

In another further embodiment of this filter apparatus, the filtration devices associated with the satellite reservoirs may comprise a sequence of barriers. Further, at least one of the barriers may be a zwitterionic barrier. In another further embodiment of this filter apparatus, at least one of the barriers in the sequence of barriers may be a membrane or may be particulate matter comprising a selective ligand. Further, the membrane or particulate matter may be positioned between the zwitterionic barrier and the satellite reservoir.

In another further embodiment of this filter apparatus, the filtration devices associated with the satellite reservoirs may comprise a sequence of barriers. Further, at least one of the barriers may be a zwitterionic packed particulate material. In another further embodiment of this filter apparatus, the particulate material may have an irregular or spherical shape. Additionally or alternatively, the particulate material may be formed of a polymeric material or a composite material.

In another further embodiment of this filter apparatus, the filter apparatus may also include: at least one cut-off membrane positioned between at least one electrode and the satellite reservoir associated therewith. Further, the cut-off membrane may be impermeable to molecules greater than 500 Daltons.

In another further embodiment of this filter apparatus, the filter apparatus may also include: a power source comprising two oppositely charged poles. Further, one of the poles may be connected to the first and third electrodes and the other pole may be connected to the second and fourth electrodes.

In another further embodiment of this filter apparatus, the electrodes may be separated from the central reservoir by a distance of no more than about 1 cm, no more than about 5 cm, no more than about 10 cm, no more than about 15 cm, no more than about 20 cm, no more than about 30 cm, no more than about 35 cm, no more than about 40 cm, no more than about 45 cm, or no more than about 50 cm.

In another further embodiment of this filter apparatus, the filter apparatus may also include: a sample in the central reservoir, the sample comprising amphoteric molecules. In another further embodiment of this filter apparatus, the amphoteric molecules may comprise proteins.

In another further embodiment of this filter apparatus, the filtration devices may have pI-selectivity values that differ from each other in increments selected from the group consisting of about 0.001 pH unit, about 0.01 pH unit, about 0.1 pH unit, and about 1.0 pH unit.

In another further embodiment of this filter apparatus, the central reservoir may be configured to rotate or may be configured to stir a sample therein.

In another further embodiment of this filter apparatus, the filtration devices may be membranes formed of a polyacrylamide gel to which an acrylamido buffer is covalently linked.

In another further embodiment of this filter apparatus, each of the filtration devices may comprise an isoelectric bead bed or substantially porous particle body.

In another further embodiment of this filter apparatus, after n separation steps, 2n+1 samples may be isolated based on pI value.

Another embodiment of the present invention addresses a method of filtering a sample provided in a central reservoir, wherein the central reservoir is in fluid communication with at least a first and a second satellite reservoir, wherein first and second portals respectively join the first and second satellite reservoirs and the central reservoir, wherein filtration devices are positioned in at least the first and second portals, wherein the filtration device in the first portal is either a highest-pI-selective or a lowest-pI-selective filtration device, and wherein the filtration device in the second portal is the other of the highest-pI-selective or the lowest-pI-selective filtration device. This method includes, among other possible steps: (a) performing a first separation step that includes, among other steps: (i) charging a first electrode in electrical contact with the first satellite reservoir; (ii) charging a second electrode in electrical contact with the second satellite reservoir, wherein the first and second electrodes are oppositely charged; and (iii) moving molecules through the highest-pI-selective and lowest-pI-selective filtration devices and into the first and second satellite reservoirs.

In a further embodiment of this method, the central reservoir may be in fluid communication with a third and a fourth satellite reservoir. Further, third and fourth portals respectively may join the third and fourth satellite reservoirs to the central reservoir. Further, filtration devices may be positioned in the third and fourth portals. Further, the filtration in the third portal may be either a higher-pI-selective or a lower-pI-selective filtration device. Further, the filtration device in the fourth portal may be the other of the higher-pI-selective or the lower-pI-selective filtration device. In addition, the method may also include the step of: (b) de-charging the first and second electrodes; and (c) performing a second separation step that includes, among other possible steps: (i) charging a third electrode in electrical contact with the third satellite reservoir; (ii) charging a fourth electrode in electrical contact with the fourth satellite reservoir, wherein the third and fourth electrodes are oppositely charged; and (iii) moving molecules through the higher-pI-selective and lower-pI-selective filtration devices and into the third and fourth satellite reservoirs.

In another further embodiment of this method, the method may also include the step of: (b) rotating or stirring the sample.

In another further embodiment of this method, at least one of the filtration devices may be a zwitterionic barrier.

In another further embodiment of this method, at least one of the filtration devices may comprise a zwitterionic packed particulate matter. In another further embodiment of this method, the particulate material may have an irregular or spherical shape. Additionally or alternatively, the particulate material may be formed of a polymeric material or a composite material.

In another further embodiment of this method, at least one of the filtration devices may be formed of a polyacrylamide gel to which an acrylamido buffer is covalently linked.

In another further embodiment of this method, at least one of the filtration devices may comprise an isoelectric bead bed or substantially porous particle body.

In another further embodiment of this method, the method may comprises n separation steps. Further, after the n separation steps, 2n+1 samples may be isolated based on pI value.

Another embodiment of the present invention addresses a kit apparatus that includes, among other possible things: (a) a central reservoir configured to contain a sample; (b) at least a first, a second, a third, and a fourth satellite reservoir in fluid communication with the central reservoir; (c) at least a first, a second, a third, and a fourth portal joining at least the first, second, third and fourth satellite reservoirs with the central reservoir; (d) at least a first, a second, a third, and a fourth filtration device, differing from each other in pI-selectivity, wherein the first, second, third, and fourth filtration devices are configured to be positioned in the first, second, third, and fourth portals, respectively, wherein the first filtration device is either a highest-pI-selective or a lowest-pI-selective filtration device and the second filtration device is the other of the highest-pI-selective or the lowest-pI-selective filtration device, and wherein the third filtration is either a higher-pI-selective or a lower-pI-selective filtration device and the fourth filtration device is the other of the higher-pI-selective or the lower-pI-selective filtration device; and (e) at least a first electrode configured to be in electrical contact with the first satellite reservoir, a second electrode configured to be in electrical contact with the second satellite reservoir, a third electrode configured to be in electrical contact with the third satellite reservoir, and a fourth electrode configured to be in electrical contact with the fourth satellite reservoir, wherein the first and the second electrodes are oppositely charged, wherein the first and the second satellite reservoirs are oppositely positioned across the central reservoir, wherein the third and the fourth electrodes are oppositely charged, and wherein the third and the fourth satellite reservoirs are oppositely positioned across the central reservoir. In a first separation step, the first and second electrodes are configured to be charged so that molecules move through the highest-pI-selective and lowest-pI-selective filtration devices and into the first and second satellite reservoirs. After the first separation step, the first and second electrodes are configured to be de-charged and the third and fourth electrodes are configured to be charged so that molecules move through the higher-pI-selective and lower-pI-selective filtration devices and into the third and fourth satellite reservoirs, thereby leaving molecules having pI values between the pI-selectivities of the higher-pI-selective and lower-pI-selective filtration devices in the central reservoir.

These and other features, aspects, and advantages of the present invention will become more apparent from the following description, appended claims, and accompanying exemplary embodiments shown in the drawings.

DETAILED DESCRIPTION OF PREFERRED EMBODIMENTS

Figure 1:
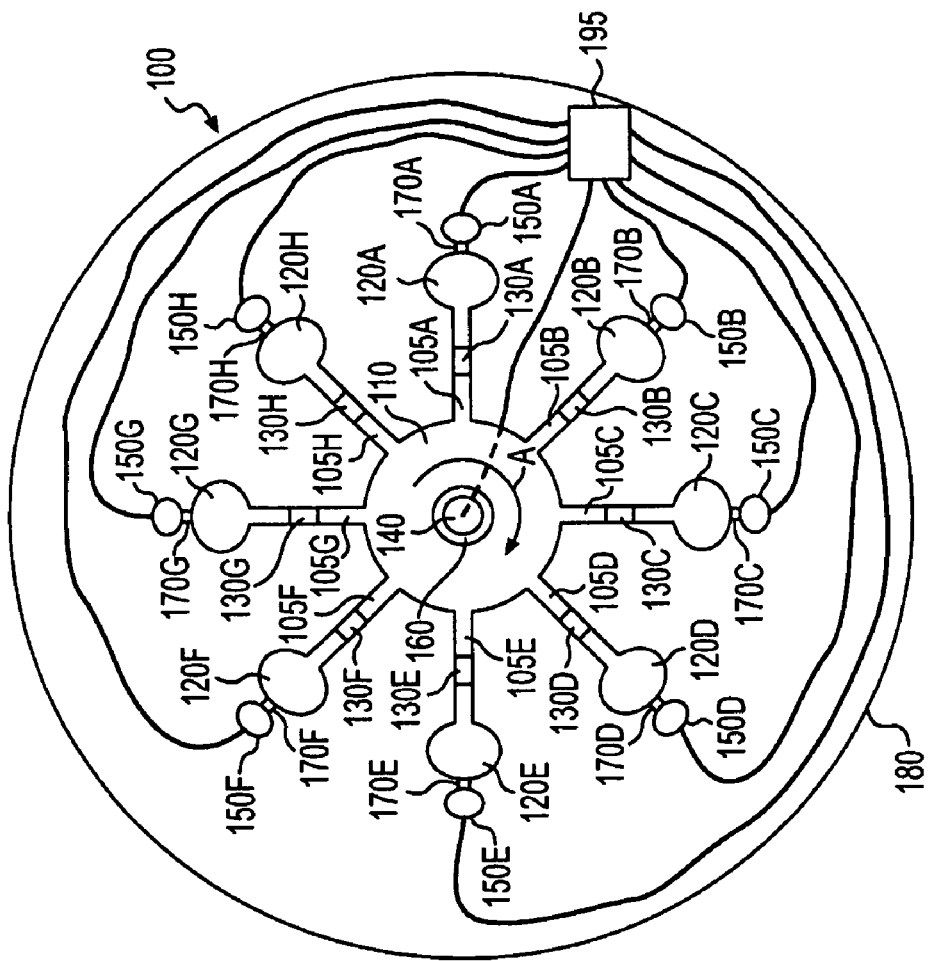
FIG. 1 is a top view of a first embodiment of a filter apparatus according to the present invention in which a central reservoir is connected to a plurality of satellite reservoirs, the apparatus is configured to separate a fluidic sample in the central reservoir into the satellite reservoirs sequentially.

Presently preferred embodiments of the invention are illustrated in the drawings. An effort has been made to use the same, or like, reference numbers throughout the drawings to refer to the same or like parts.

This invention enables amphoteric molecules, e.g., proteins to be very quickly filtered, separated, concentrated, fractionated, and/or fixated (hereinafter collectively referred to as "filtered") based on one or more molecular properties such as, for example, pI value. In one embodiment, the present invention filters, in "electro-filtration modes," molecules illustrated by proteins mixtures, various molecules from cell extracts, peptides, and other samples or salts. This embodiment uses electrophoresis principles, such as carrier-free isoelectric focusing, as filtration principles. Another embodiment of the invention uses centrifugal force coupled with pI-selective filtration devices to filter a sample. In addition, another embodiment isolates a sample having pI values in a middle portion of a range of pI values.

The first embodiment of the invention is shown in FIG. 1. This embodiment employs an apparatus 100 which includes a base 180 which houses a central reservoir 110, a plurality of satellite reservoirs 120A-H, and a plurality of portals 105A-H which connect the central reservoir 110 to the satellite reservoirs 120A-H.

The central reservoir 110 has an inlet (not shown) for receiving a fluidic sample which may be, for example, a solution containing amphoteric molecules such as protein molecules having a variety of pI values. The central reservoir 110 is electrically connected to a first electrode 140 which may be provided in a central portion of the central reservoir 110. However, as molecules, such as proteins, in a sample in the central reservoir 110 may become denatured and/or precipated out of solution if they contact the first electrode 140, the first electrode 140 may be insulated from the sample by means of a cut-off membrane 160. The cut-off membrane 160, which may substantially surround the first electrode 140, may be permeable to small ions but impermeable to the molecules to be protected. For example, the cut-off membrane 160 may be permeable to molecules smaller than 500 Daltons and impermeable to molecules greater than 500 Daltons. As a result of the ion flow through the cut-off membrane 160, charge may be transferred from the first electrode 140 through the fluid in the central reservoir 110.

The central reservoir 110 may be configured to rotate such as, for example, in the clockwise direction (indicated by arrow "A") or in a counterclockwise direction. Similarly, a sample provided in the central reservoir 110 may also rotate. For example, the sample may be stirred by means of (a) a magnetic stirring ball placed in the central reservoir 110 which may react to an external magnetic drive or (b) a piezoelectric oscillator which may be positioned adjacent the central reservoir 110 to generate oscillatory waves. In addition, one or more rotary impellers could be located in the central reservoir 110 which would not only mix the sample but also would drive it toward the portals 105A-H.

Filtration devices 130A-H are configured to be positioned in each of the portals 105A-H, respectively. Each filtration device 130A-H may comprise one barrier or a sequence of two or more barriers arranged in series. For example, the filtration devices 130A-H may be, for example, zwitterionic barriers. By way of further example, the filtration devices 130A-H may be a membranes, isoelectric bead beds, or be formed of particulate matter comprising a selective ligand. Preferably, if the filtration devices 130A-H comprise a membrane or particulate matter, the membrane or particulate matter will be positioned between the satellite reservoir 120A-H and a zwitterionic barrier provided in the respective portal 105A-H. If the filtration devices 130A-H comprise particulate matter, the particulate matter may be zwitterionic packed particulate material. Moreover, the particulate material may be either irregularly shaped or spherically shaped. In addition, the particulate material may be formed of either polymeric material or a composite material.

By way of further example, if the filtration devices 130A-H are membranes, the membranes may be formed of a polyacrylamide gel to which an acrylamido buffer is covalently linked, thereby fixing the buffering pH of the gel at any desired value. Further, the membranes may be, for example, monofilament screens, gels, fritted discs, etc.

Once an electric field is applied to a pH buffered polyacrylamide membrane (for example, by energizing oppositely charged electrodes 140, 150 positioned on opposite ends of the membrane), the membrane becomes pI-selective. In other words, the membrane will only allow amphoteric molecules, e.g., proteins, to move through it towards an oppositely charged electrode if the molecules have pI value which is greater than or equal to the pI-selectivity value of the membrane.

The filtration devices 130A-H may also comprise a substantially porous particle body having a plurality of cavities extending inwardly from the surface thereof. The particle body may further comprise a substance of predetermined isoelectric point such that said particle maintains a substantially neutral electrostatic charge at a predetermined pH. In one embodiment, the particles may have sizes, mechanical strengths, and buoyancies that are compatible with separating biological materials. In more specific embodiments, the particle bodies may be made using materials such as one or more mineral oxides, or, alternatively, a plastic bead that is sufficiently porous so that a polymer can be introduced inside the particle body.

Polystyrene is a well known polymer that can be formed into beads having pores for chromatography. Other synthetic polymers that are useful in the present invention are those based on acrylics such as methymethacrylates, porous nylons, porous polyvinyl plastics, and polycarbonates. Still others will be familiar to those having skill in the polymer arts. In still more specific embodiments, the materials may comprise one or more mineral oxides including, but not limited to, a trivalent mineral oxide such as: aluminum, gallium, indium, scandium, yttrium, lanthanum, actinium, or a rare earth mineral; or a tetravalent mineral oxide such as titania, zirconia, or hafnia. Examples of suitable porous particle bodies that can be used in the practice of the invention include the porous particle bodies described in U.S. Pat. Nos. 6,613,234; 5,470,463; 5,393,430; and 5,445,732. Suitable particles are sold under the trade names HYPERD™ and HYPERZ™ by Ciphergen Biosystems of Fremont, Calif.

Thus, in one aspect, the present invention provides a method of making composite particles with a predetermined isoelectric point. In one embodiment, the method may comprise the steps of: selecting monomers and their quantities to obtain upon polymerization a cross-linked polymer having the predetermined isoelectric point; preparing a solution of the monomers; contacting the monomer solution with particles having porous particle bodies in which the particle bodies are dimensioned to allow fluid entry into the particles; and reacting the monomers under conditions effective to form the polymer having said predetermined isoelectric point within the porous particle bodies to form thereby composite particles with a predetermined isoelectric point. Exemplary teachings can be found in U.S. Pat. Nos. 6,613,234, 5,470,463, 5,393,430, and 5,445,732.

In some embodiments, the particles may have diameters between about 10 μm and about 200 μm, and, in more specific embodiments, the particles may have pore volumes greater than about 40% of the total particle volumes, and, still more specifically, greater than about 50% of the total particle volume. In some embodiments, monomers may be selected from the group consisting: N-acryloylglycine, 4-acrylamidobutyrric acid, 2-morpholinoethylacrylamide, 3-morpholinopropylacrylamide, N,N-dimethylaminoethylacrylamide, N,N-dimethylaminopropylacrylamide. In other embodiments, the particles may comprise zirconium oxide. In addition, a poration agent can be optionally use as well. For example, one can add a pore-inducing agent such as polyethyleneglycol 6000 at a concentration between about 8% and about 20%. The particles can also optionally be coated with known passivating agents such as described in published U.S. patent application Ser. No. 2002-0005383 A1.

In some embodiments of the invention, a substance having a predetermined isoelectric point may be deposited in said cavities of said particle. More particular embodiments include those in which the substance is a polymer having a predetermined isoelectric point. In still more specific embodiments, the polymer may be polyacrylamide or the polymer may be a block copolymer. Such embodiments can be prepared using materials and methods familiar to those having skill in the arts of polymer chemistry and biochemistry. For example, suitable isoelectric substances can be made by combining acrylamide monomers and immobilines in amounts and under conditions that are effective to produce a polymer having a defined isoelectric point. Briefly, as known to those of skill in the art of bioanalytical chemistry and as described in U.S. Pat. No. 4,971,670 to Faupel, et al., immobilines are acrylamide derivatives having the general formula:

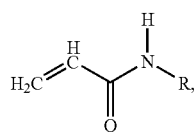

where R includes a group that provides the characteristic pI. While there are many molecules that are embraced by this description, one collection for creating isoelectric gels is commercialized by Amersham under the trade name IMMOBILINE™. This collection includes the following molecules ("immobilines") having the indicated pI: N-acryloylglycine (pK 3.6); 4-acrylamidobutyrric acid (pK 4.6); 2-morpholinoethyl-acrylamide (pK 6.2); 3-morpholinopropylacrylamide (pK 7.0); N,N-dimethylaminoethylacrylamide (pK 8.5); and N,N-dimethylaminopropylacrylamide (pK 9.3). These monomers may be combined and co-polymerized with acrylamide and N,N-methylenebisacrylamide, or other suitable cross-linking agent, to produce the desired pI specific polymer. Methylacrylamide can be substituted for acrylamide.

Compositions of desired pI can be derived by combining immobilines and co-polymerizing agents using available software, such as "Doctor pH" (available from Amersham, Uppsala, Sweden at www.amersham.com) according to the information provided under the title "Isoelectric membrane formulas for isoprime purification of proteins".

Methods for determining the value of pI for various macromolecules are known. Examples of such methods include: Ribeiro, J, M. and Sillero, A., "An algorithm for the computer calculation of the coefficients of a polynomial that allows determination of isoelectric points of proteins and other macromolecules", COMPUTERS IN BIOLOGY & MEDICINE 20(4):235-42 (1990); Ribeiro, J. M. and Sillero, A., "A program to calculate the isoelectric point of macromolecules" COMPUTERS IN BIOLOGY & MEDICINE 21(3):131-41 (1991); and Sillero, A. and Ribeiro, J. M., "Isoelectric points of proteins: theoretical determination" ANALYTICAL BIOCHEMISTRY 179(2):319-25 (1989). Such methods can be used to determine the pI value for the polymers described herein.

For example and without limitation, particles having defined isoelectric points in accordance with the present invention can be prepared in accordance with the specific examples provided in Example Section below. In summary, as illustrated by Example 1, aqueous solutions of acrylamide monomers effective to provide a desired pI may be combined with the appropriate cross-linking reagents and polymerization catalysts may be combined in a slurry with the above-described particles in proportions sufficient to cause polymerization of the acrylamides within the cavities of the particles as described in greater detail in the '234 and '763 patents, to create thereby particles having a defined pI.

In other embodiments, the substance of predetermined isoelectric point may be deposited on said interior and exterior surfaces of the particle (i.e., the interior and exterior particle surfaces formed by the interior pore volume of above-described cavities). The deposition can be by chemical bond or other means. Amino acids may be useful to provide such surface layers, as amino acids have defined isoelectric points. Thus, in some embodiments, the substance may comprise an amino acid; and, in more specific embodiments, the substance may comprise two or more amino acids.

The amino acid can be any of the twenty naturally-occurring amino acids, or the amino acid can be a unnatural amino acid. More specifically, useful amino acids include those among the twenty naturally occurring amino acids having ionizable side chains, including: lysine, arginine, glutamic acid, aspartic acid, serine, cysteine, threonine, tyrosine, asparagines, glutamine. In addition, it will be understood by those of skill in the biochemistry arts that other compounds having defined pI values that can be attached to the interior and exterior particle surfaces as described above can be used with the present invention. Linkers may be used to provide attachment sites on the surface of the particle. Suitable linker chemistry will be familiar to those of skill in the art of surface chemistry.

One example describing the formation of amino acid modifications to particle surfaces in provided in Example 6 below. Porous zirconia beads filled with agarose hydrogel are first reacted with sodium hydroxide (NaOH) and allyl bromide ($CH_2CH_2CH_2Br$) to produce particle surfaces having allyloxy groups attached thereon. The allyloxy groups are further brominated to form 3-bromopropyloxy surface linkers that are subsequently reacted with lysine to provide particles having lysine-linked surfaces with a particle pI value of 8.2.

In other embodiments, the above-described particles may further produce substantially zero electroendoosmotic force. In some of these embodiments, the particle may comprise a material substantially incapable of producing an electroendoosmotic force, and, in more particular embodiments, the material may be polystyrene. In other such embodiments, the particles may be formed from two or more materials having substantially equal and opposing electroendoosmotic effects to form thereby particles of substantially zero electroendoosmotic force. Examples of these embodiments include particles having mineral oxides provided in proportions effective to render said particle substantially incapable of producing an electroendoosmotic force. Examples of suitable mineral oxides chosen from the group consisting of: zirconia, silica, titania, alumina, and mixtures thereof.

In still other embodiments, the particle may comprise a base material that produces a first electroendoosmotic force and said base material may be substantially coated with a substance that produces an electroendoosmotic force that is substantially equal and opposite to said first electroendoosmotic force so that said particle produces a substantially zero electroendoosmotic force. Thus, the present invention provides methods and materials for modifying the electroendoosmotic properties of the particles described herein to provide particles having a substantially zero electroendoosmotic force.

Examples of suitable particle-coating combinations include particles in which the base material is silica and said substance is a polycationic hydrophilic polymer and particles in which the base material is zirconia and said substance is a polyanionic hydrophilic polymer. In addition, one or more amino acids suitable polymers can be used to provide the desired compensatory surface layer. Polymers used to coat the mineral oxide and, therefore, reduce the electroendoosmosis level close to zero may be light ionic soluble polymers with a complementary charge. For silica-based beads, for instance, the polymer can be an amino-containing polymer such as a DEAE dextran. In practice, the polymer may be put in contact with the silica beads for suitable period of time, and the polymer excess may be eliminated by an extensive washing with water. Only the required amount of cationic dextran capable to counterbalance the acidic character of silica will remain with the beads. For zirconium oxide, where the overall charge of the material is positive, appropriate polymers are those that weak acids such as carboxyl groups. The amount of coating polymer may be chosen so that the net charge of the resulting composite material is approximately zero.

Regardless of the type of filtration devices 130A-H used in the portals 105A-H, the filtration devices 130A-H differ in pI-selectivity. For example, the filtration devices 130A-H may differ in pI-selectivity in increments of about 0.001 pH unit, about 0.01 pH unit, about 0.1 pH unit, or about 1.0 pH unit.

As a result of the varying pI-selectivity, the filtration devices 130A-H in each portal 105A-H are configured to pass a different set of molecules to each of the respective satellite reservoirs 120A-H. To facilitate the passage of the molecules through the filtration devices 130A-H into the satellite reservoirs 120A-H, the each satellite reservoir 120A-H is electrically connected to a respective second electrode 150A-F. The second electrodes 150A-F may be provided in their respective satellite reservoirs 120A-F. Or, similar to the first electrode 140, each of the second electrodes 150A-F may be insulated by a respective cut-off membrane 170A-F. The second electrodes 150A-F are configured to have an opposite charge than the first electrode 140. In addition, a power source and/or a switching device 195 may be provided to charge and de-charge each of the second electrodes 150A-H sequentially. Further, the switching device 195 may also be configured to charge and de-charge the first electrode 140.

In operation, a sample containing amphoteric molecules having varying pI values is provided in the central reservoir 110. The switching device 195 oppositely charges the first electrode 140 and a primary second electrode 150A, to create an electromagnetic field between the first electrode 140 and the primary second electrode 150A. For example if the first electrode is positively charged (as a cathode) and the primary second electrode 150A is negatively charged (as an anode), molecules in the sample, having pI values greater than the pI-selectivity of the filtration device 130A will move through the portal 105A and into the satellite reservoir 120A associated with the primary second electrode 150A. The remaining molecules, i.e., molecules having pI values less than the pI-selectivity of the filtration device 130A in the portal 105A will remain in the central reservoir 110.

After all of the molecules in the sample having pI values greater than the pI-selectivity of the filtration device 130A in the first portal 105A have moved into the first satellite reservoir 120A, the switching device 195 may be configured to de-charge the primary second electrode 150A and to charge a secondary second electrode 150B. At this time, molecules in the sample having pI values greater than the pI-selectivity of the filtration device 130B associated with the secondary second electrode 150B will pass through the portal 105B and into the associated satellite reservoir 120B. As a result, the molecules in the satellite reservoir 120B associated with the secondary second electrode 150B will have pI values between the pI-selectivities of the filtration devices 130A, 130B in the first and second portals 105A, 105B.

After all of the molecules in the sample having pI values greater than the pI-selectivity of the filtration device 130B in the second portal 105B have moved into the second satellite reservoir 120B, the switching device 195 may be configured to de-charge the secondary second electrode 150B and to charge a tertiary second electrode 150C. At this time, molecules in the sample having pI values greater than the pI-selectivity of the filtration device 130C associated with the tertiary second electrode 150C will pass through the portal 105C and into the associated satellite reservoir 120C. As a result, the molecules in the satellite reservoir 120C associated with the tertiary second electrode 150C will have pI values between the pI-selectivities of the filtration devices 130B, 130C in the second and third portals 105B, 105C.

This process is sequentially repeated for each of the remaining second electrodes 150D-H. After the final second electrode 150H is decharged, the molecules of the original sample in the central reservoir 110 will be distributed as follows: (a) molecules having pI values greater than the pI-selectivity of the first filtration device 130A will be in the first satellite reservoir 120A; (b) molecules having pI values between the pI-selectivities of the first and second filtration devices 130A, 130B will be in the second satellite reservoir 120B; (c) molecules having pI values between the pI-selectivities of the second and third filtration devices 130B, 130C will be in the third satellite reservoir 120C; (d) molecules having pI values between the pI-selectivities of the third and fourth filtration devices 130C, 130D will be in the fourth satellite reservoir 120D; (e) molecules having pI values between the pI-selectivities of the fourth and fifth filtration devices 130D, 130E will be in the fifth satellite reservoir 120E; (f) molecules having pI values between the pI-selectivities of the fifth and sixth filtration devices 130E, 130F will be in the sixth satellite reservoir 120F; (g) molecules having pI values between the pI-selectivities of the sixth and seventh filtration devices 130F, 130G will be in the seventh satellite reservoir 120G; (h) molecules having pI values between the pI-selectivities of the seventh and eighth filtration devices 130G, 130H will be in the eighth satellite reservoir 120H; and (i) molecules having pI values less than the pI-selectivity of the eighth filtration device 130H will remain in the central reservoir 110.

In the above-described embodiment, the first electrode was negatively charged (i.e., as an anode) and the second electrodes 150A-H were sequentially positively charged (i.e., as cathodes). Of course, the charges can be switched and in such a case the order of separation would be reversed, i.e., molecules having pI values less than the pI-selectivity of the eighth filtration device 130H would move into the eighth satellite reservoir 120H followed by the sequential separation into the remaining satellite reservoirs 120G, 120F, 120E, 120D, 120C, 120B, 120A.

The electrodes 140, 150A-H, which may be formed of any conductive material such as, for example, gold, platinum, iridium, dioyde, etc., need not take any particular form. For example, each of the electrodes 140, 150A-H may be in the form of a rod, a plate, etc.

Various alterations and/or additions to the apparatus 100 are within the scope of the embodiment. For example, although shown as being equidistant, the distance between the central reservoir 110 and the satellite reservoirs 120A-H may vary. Preferably, the distance between the central reservoir 110 and the satellite reservoirs 120A-H is small. Of course, the smallest distance would be if the central reservoir 110 and the satellite reservoirs 120A-H were merely separated by membrane filtration devices 130A-H having negligible thicknesses.

The size of the satellite reservoirs 120A-H may also vary. As a result, the concentration of the molecules passing into the satellite reservoirs 120A-H may correspondingly vary, thereby enabling the molecules to be diluted or concentrated as desired.

The distance between the first electrode 140 and the second electrodes 160A-H may also vary. For example, the distance between the first electrode 140 and the second electrodes 160A-H may be no more than about 1 cm, no more than about 5 cm, no more than about 10 cm, no more than about 15 cm, no more than about 20 cm, no more than about 30 cm, no more than about 35 cm, no more than about 40 cm, no more than about 45 cm, or no more than about 50 cm.

The apparatus 100 may be combined with one or more external devices. For example, the apparatus 100 could be combined with a mechanical device which removes the contents of each of the satellite reservoirs 120A-H and/or the central reservoir 110 upon completion of the filtration. In addition, each of the satellite reservoirs 120A-H could be connected to a diagnostic device which tests or confirms the contents of the satellite reservoirs upon completion of the filtration. Similarly, the satellite reservoirs 120A-H could be adjacent biochips onto which the contents of the satellite reservoirs 120A-H can be deposited for analysis.

The satellite reservoirs 120A-H may contain selected materials (e.g., beads) which bind to certain types of molecules (e.g., proteins). For example, the material could be (a) beads with magnetized cores which are easily removable by means of a magnet, (b) beads having an ion exchange function group, affinity function group, or Hydrophobic Interaction Chromatography ("HIC") function group which covalently bond to certain charged molecules, or (c) other material.

As previously discussed, the filtration devices 130A-H may be one or more barriers such as, for example, membranes, bead beds, or particulate matter comprising a selective ligand. In addition, however, the types of filtration devices 130 within a portal 105A-H may also vary. For example, a combination of membranes and isoelectric bead beds may be used as the filtration device 130 in a portal 105. Further, a combination of isoelectric bead beds formed by different techniques may be used, e.g., beads having different particle sizes or constitutions. Similarly, more than one type of membrane may be used, e.g., a pI-selective membrane may be coupled with a size selective membrane (or similar net or frit), a hydrophobic membrane, a hydrophilic membrane, a charged membrane, a chemically reactive membrane, etc. In other words, any combination of the aforementioned type of filtration devices may be combined to create the filtration device 130 in a portal 105.

By way of further explanation, a size-selective membrane may enable molecules having sizes smaller than its pore size to pass through while blocking or trapping molecules having sizes larger than its pore size. Further, if the membrane were hydrophobic, it would trap hydrophobic amphoteric molecules and repel hydrophilic amphoteric molecules, thereby separating the hydrophobic molecules from the hydrophilic molecules. By way of contrast, if the membrane were hydrophilic, it would repel hydrophobic molecules while allowing other molecules to pass through it. It should be understood that hydrophobic membranes are distinguishable from hydrophilic membranes in that the former have exposed clusters of hydrophobic molecules that confer adsorption properties for hydrophobic solid supports, whereas hydrophilic membranes are enabled to allow hydrophilic molecules to pass through the membrane. If the membrane were charged, the membrane would block molecules having a opposite charge while allowing molecules having the same charge to pass through it. Finally, membranes having a reactive chemical composition may react with certain molecules thereby trapping them while allowing other molecules to pass through it. Of course, any of these additional membranes may be used in succession.

In addition, the apparatus 100 may include a heating/cooling element (not shown) to control the temperature of the fluid to be filtered and/or the buffer solution in the reservoirs 110, 120A-H. In addition, the apparatus 100 may also include other monitoring devices or controls. For example, an optical control (not shown) may be provided to emit light (e.g., IR, laser, etc.) into one or more of the reservoirs 110, 120A-H. The intensity of light which is reflected off the sample to be filtered and/or a buffer solution may be used to determine and/or control various fluid properties such as, for example, the concentration thereof.

Figure 2:
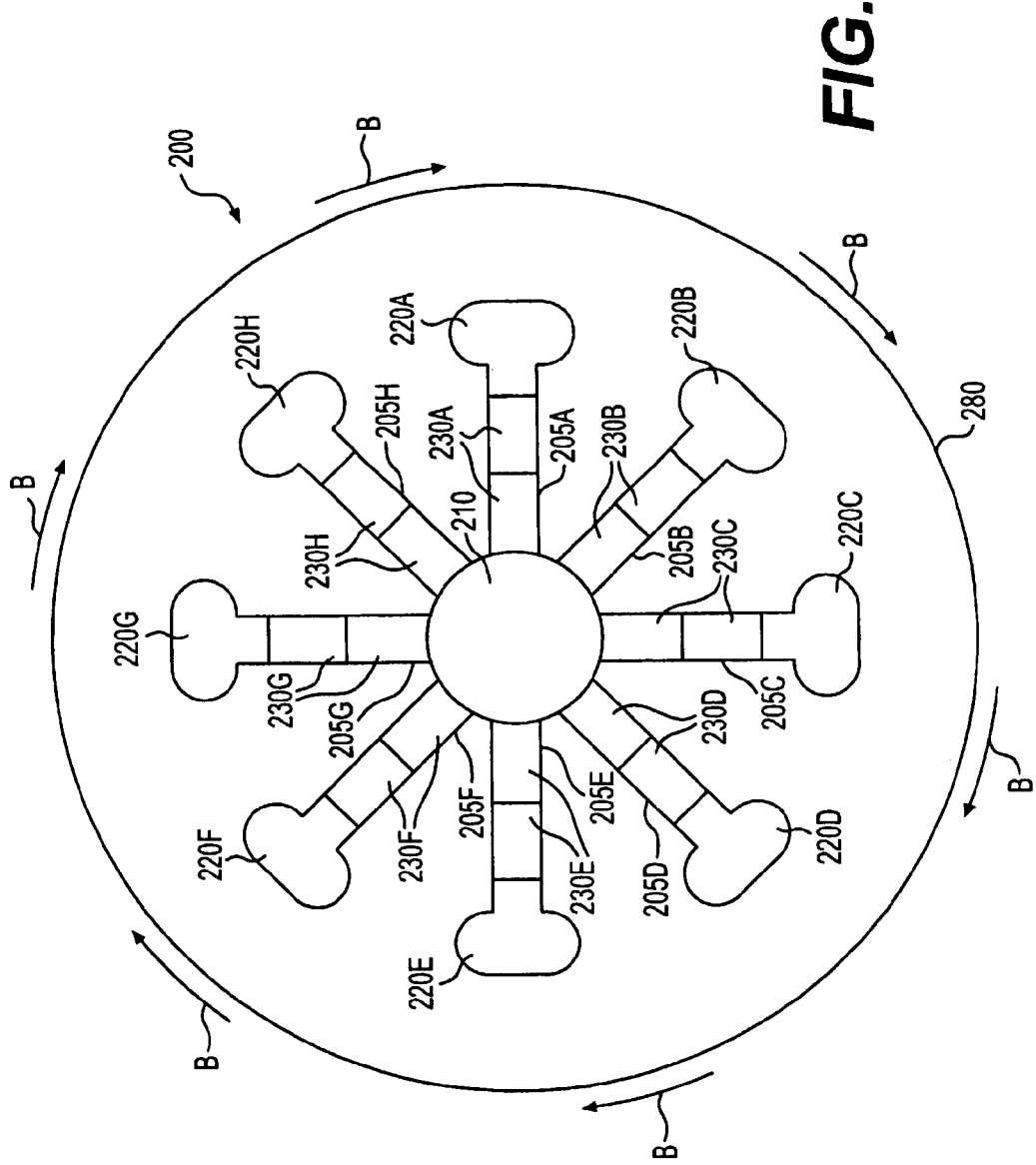
FIG. 2 is a top view of a second embodiment of a filter apparatus according to the present invention in which a central reservoir is connected to a plurality of satellite reservoirs, the apparatus is configured to separate a fluidic sample in the central reservoir into the satellite reservoirs by means of centrifugal separation.

FIG. 2 shows an apparatus 200 according to a second embodiment of the invention. Similar to the apparatus 100 of the first embodiment, this apparatus 200 includes base 280 which houses a central reservoir 210 and a plurality of satellite reservoirs 220A-H connected to the central reservoir 210 by means of a plurality of respective portals 205A-H. However, rather than use electrodes 140, 160, this apparatus 200 employs centrifugal force to filter a sample provided in the central reservoir. Specifically, the apparatus 200 is configured to rotate either in a clockwise direction (indicated by arrows "B") or in a counterclockwise direction.

As the apparatus 200 rotates, a sample provided in the central reservoir 210 moves radially outward toward the satellite reservoirs 220. However, passage to the satellite reservoirs 220 is inhibited by filtration devices 230A-H provided in the portals 205A-H.

The filtration devices 230A-H may be similar to the filtration devices 130A-H of the first embodiment, both in the type of filtration devices and in the number of filtration devices provided in each portal 205A-H (i.e., a singular filtration device or a series of filtration devices may be provided in the portals 205A-H).

In addition, however, the filtration devices 230A-H of this embodiment may contain columns preferentially filled with different sorbents that are configured to capture different molecules, (e.g., protein molecules) based on molecular affinity properties such as, for example, pI-selectivity. As a result, a thoroughly mixed sample provided in the central reservoir will be driven to each satellite reservoir and each filtration device 203A-H will adsorb a different set of molecules.

Upon completion of the filtration, molecules of interest may be removed from the satellite reservoirs 220A-H and/or from the filtration devices 230A-H. The molecules of interest could be isolated from the filtration devices 230A-H, for example, by means of being washed with a physiological buffer and/or a solvent mixture adapted to desorb the molecules (e.g., proteins) from the filtration devices 230A-H. Moreover, like the previously described apparatus 100, the identified molecules of interest in this apparatus 200 may be automatically moved to wells, biochips, etc. for further analysis. Similarly, the volume of the satellite reservoirs 220A-H and/or filtration devices 230A-H may vary so that the resultant concentration of the molecules of interest can be controlled.

Other variations of this apparatus 200 may include providing affinity ligands in (or as) the filtration devices 230A-H. The affinity ligands may be selected against families of molecules (e.g., proteins) in a sample in the central reservoir 210. Further, the affinity ligands could be antibodies.

In another variation, the central reservoir 210 may contain more than one chambers. For example, a first chamber may contain a sample which will be centrifuged first. Another chamber may then be opened, thereby centrifuging a solution (e.g., washing solution and/or elution solution, e.g., acetic acid) therein. If an elution solution is desired, various chambers could house a particular elution solution applicable to each filtration device 230A-H and satellite reservoir 220A-H associated therewith. Further, the spinning velocity and/or duration of the apparatus may be varied for each of the solutions (including the sample) to be driven through the portals 205A-H.

Figure 3:
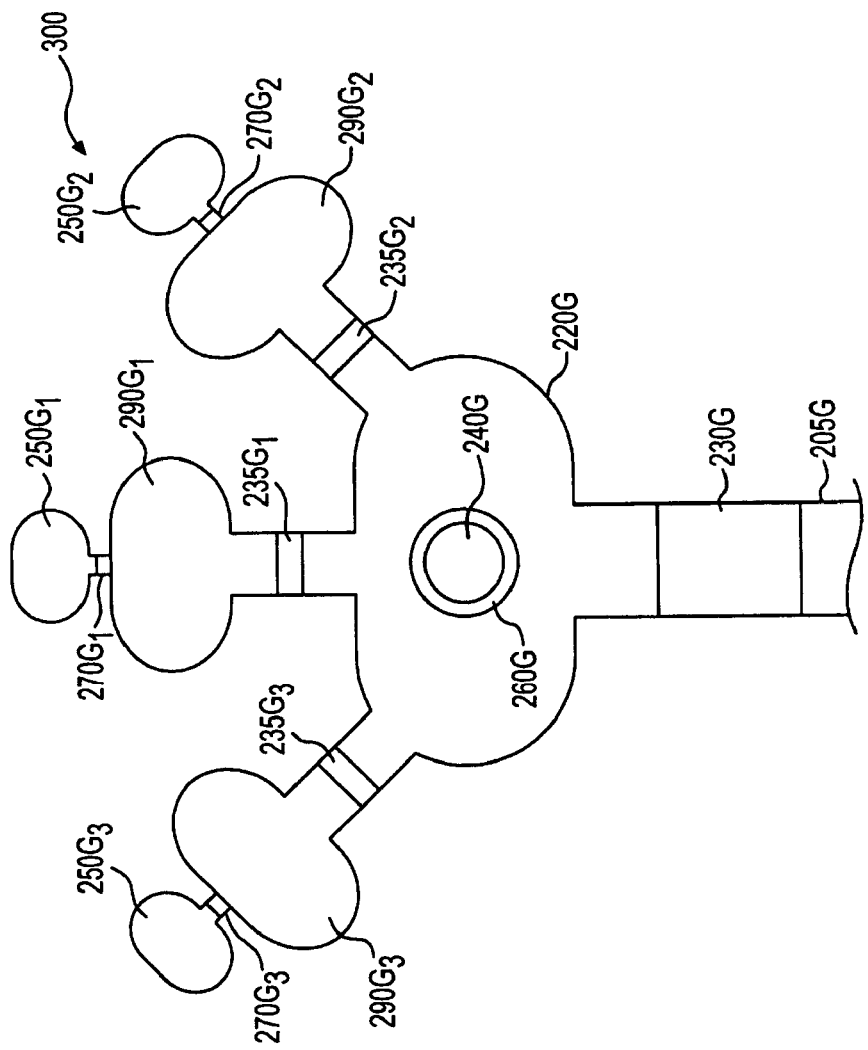
FIG. 3 is a top view of a portion of a third embodiment of the invention which combines the centrifugal aspects of the embodiment shown in FIG. 2 with the sequential separation embodiment of FIG. 1, such that one of the satellite reservoirs of FIG. 2 is connected to a further plurality of regional reservoirs which are connected to electrodes.

One particular variation of this embodiment is an apparatus 300 shown in FIG. 3. Although only one satellite reservoir 220G is shown in FIG. 3, it is to be understood that a similar structure may be associated with the other satellite reservoirs 220 of the apparatus 200 shown in FIG. 2, as this apparatus 300 combines the second embodiment apparatus 200 with the concepts of the first embodiment apparatus 100. As a result, only one satellite reservoir 220G will be discussed.

In this apparatus 300, a first electrode 240G is provided in the satellite reservoir 220G; the first electrode 240G may be insulated by means of cut-off membrane 260G. The satellite reservoir 220G is separated from a plurality of regional reservoirs $290G_1$-$G_3$ by a respective plurality of regional filtration devices $235G_1$-$G_3$ each of which has a different pI-selectivity. Each of the regional reservoirs $290G_1$-$G_3$ is in electrical contact with a respective second electrode $250G_1$-$G_3$ and may be separated therefrom by cut-off membranes $270G_1$-$G_3$. As a result, after a centrifugal separation is complete (according to the method of second embodiment apparatus 200), a solution resultant in the satellite reservoir 220G may be further filtered by means of a sequential filtration into the regional reservoirs $290G_1$-$G_3$ (according to the method of the first embodiment apparatus 100). Of course, any of the variations discussed with respect to the first and second apparatus embodiments 100, 200 apply to this apparatus embodiment 300.

Figure 4:
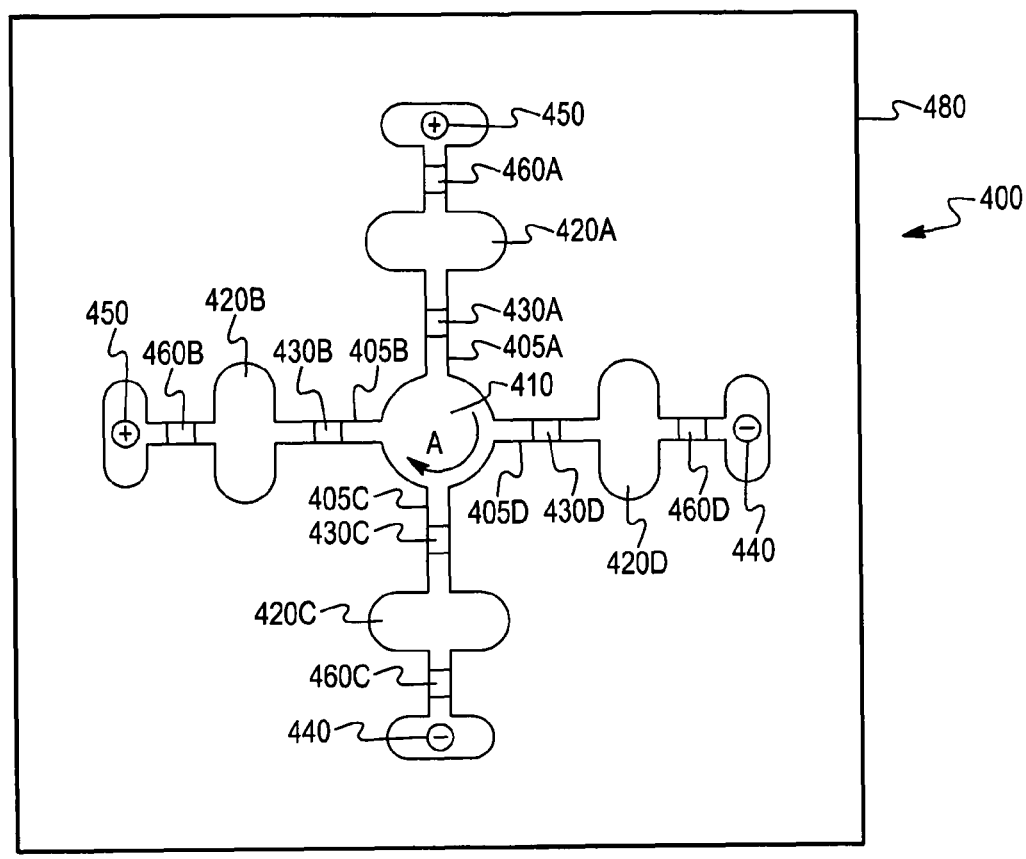
FIG. 4 is a top plan view of a separator according to a fourth embodiment of the present invention.
Figure 5:
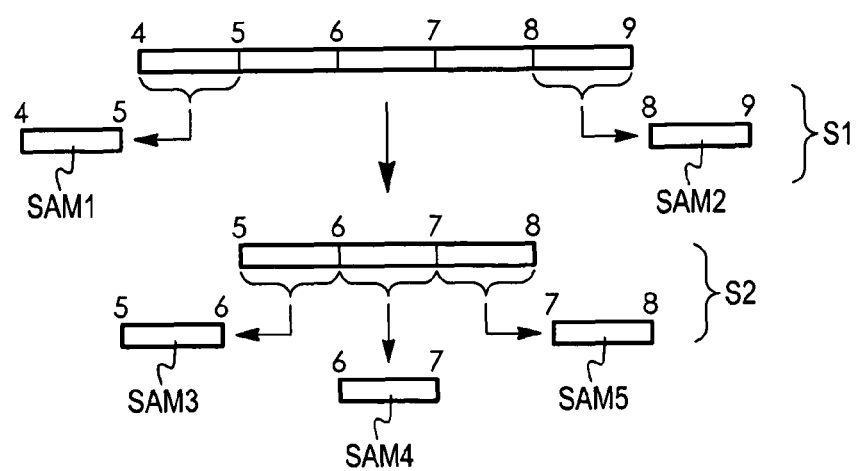
FIG. 5 is a schematic diagram which describes a separation process according to the fourth embodiment of the invention.

A fourth embodiment of the invention is shown in FIGS. 4 and 5. Similar to previous embodiments, the separator 400 according to this embodiment includes a central reservoir 410 and a plurality of satellite reservoirs 420A-D, the number of which will, of course, depend on the desired separation.

This separator embodiment 400 includes a base 480 which houses: (a) the central reservoir 410; (b) the plurality of satellite reservoirs 420A-D; (c) a plurality of portals 405A-D which connect the central reservoir 410 to the satellite reservoirs 420A-D; and (d) filtration devices 430A-D (each of which may be any of the filtration devices previously discussed with respect to the other embodiments of the invention) configured to be provided in each of the portals 405A-D, respectively. The central reservoir 410 has an inlet (not shown) for receiving a fluidic sample which may be, for example, a solution containing amphoteric molecules such as protein molecules having a variety of pI values.

The filtration devices 430 differ from each other in pI-selectivity. For example, if four filtration devices 403A-D are provided, the filtration devices may be described with respect to each other as being lowest-pI-selective, lower-pI-selective, higher-pI-selective, and highest-pI-selective. Moreover, the differences in pI-selectivity may be in regular intervals. For example, the pI-selective values of the filtration devices 430A-D may differ from each other in increments of about 0.001 pH unit, about 0.01 pH unit, about 0.1 pH unit, about 1.0 pH unit, etc.

Each of the satellite reservoirs 420A-D is electrically connected to a first (e.g., positively charged) electrode 440 or a second (e.g., negatively charged) electrode 450. More specifically, half of the satellite reservoirs 420A-D (e.g., reservoirs 420C, 420D) will be connected to negatively charged electrodes 440 and the other half of the satellite reservoirs 420A-H (e.g., reservoirs 420A, 420B) will be connected to positively charged electrodes 450. The positively charged electrodes 450 are positioned opposite the reservoirs 420C, 420D connected to the negatively charged electrodes 440. Accordingly, although the first and second electrodes 440, 450 are shown as being paired in FIG. 4, this is not required. For example, if six electrodes are employed, the first and second electrodes 440, 450 could alternate around the central reservoir 410 or have some other arrangement provided that, in each instance, a positive electrode 450 is opposite a negative electrode 440.

As molecules, such as proteins, in a sample portion in the satellite reservoirs 420A-D may become denatured and/or precipated out of solution if they contact the electrode 440, 450 associated therewith, the electrodes 440, 450 may be insulated from the sample portions by means of cut-off membranes 460A-D. The cut-off membranes 460A-D, which may substantially surround the electrodes 440, 450, may be permeable to small ions but impermeable to the molecules to be protected. For example, the cut-off membranes 460A-D may be permeable to molecules smaller than 500 Daltons and impermeable to molecules greater than 500 Daltons. As a result of the ion flow through the cut-off membranes 460A-D, charge may be transferred from the electrodes 440, 450 through the fluid in the sample portions in the satellite reservoirs 420A-D.

The central reservoir 410 may be configured to rotate such as, for example, in the clockwise direction (indicated by arrow "A") or in a counterclockwise direction. Similarly, a sample provided in the central reservoir 410 may also rotate. For example, the sample may be stirred by means of (a) a magnetic stirring ball placed in the central reservoir 410 which may react to an external magnetic drive or (b) a piezo-electric oscillator which may be positioned adjacent the central reservoir 410 to generate oscillatory waves. In addition, one or more rotary impellers could be located in the central reservoir 410 which would not only mix the sample but also would drive it toward the portals 405A-D.

Similar to the separator 100 of the first embodiment, this separator 400 embodiment rotates an electric field so as to drive the separation. Specifically, in a first separation step (S1 in FIG. 5) an electrode 450 adjacent a first satellite reservoir 420A and an oppositely charged electrode 440 adjacent a second satellite reservoir 420C opposite the first satellite reservoir 420A are charged.

In this first separation step S1, the filtration device 430A in the first portal 405A is either a highest-pI-selective filtration device or a lowest-pI-selective filtration device. Similarly, the filtration device 430C in the third portal 405C is the other of the highest-pI-selective filtration device or the lowest-pI-selective filtration device. For example, the highest-pI-selective filtration device 430A may allow molecules having pI values greater than or equal to 8.0 to pass therethrough and the lowest-pI-selective filtration device 430C may allow molecules having pI values less than or equal to 5.0 to pass therethrough. For purposes of explanation, the highest-pI-selective filtration device 430A will be defined in the first portal 405A and the lowest-pI-selective filtration device 430C will be defined in the third portal 405C. As a result, after the first filtration step S1: (a) the sample in the central reservoir 410 will contain molecules having pI values between about 5.0 and about 8.0; (b) the first satellite reservoir 420A will contain molecules having pI values greater than or equal to about 8.0; and (c) the third satellite reservoir 420C will contain molecules having pI values less than about 5.0.

At this point, the first and second electrodes 440, 450 adjacent their respective satellite reservoirs 420C, 420A are de-charged. Subsequently, another pair of oppositely positioned and oppositely charged first and second electrodes 440, 450 are charged. For example, the electrode 440 adjacent one of the satellite reservoirs 420D and the oppositely charged electrode 450 adjacent the opposite satellite reservoir 420B may be charged.

In this second separation step S2, the filtration device 430B in the second portal 405B is either a higher-pI-selective filtration device or a lower-pI-selective filtration device. Similarly, the filtration device 430D in the fourth portal 405D is the other of the higher-pI-selective filtration device or the lower-pI-selective filtration device. For example, if after step S1, the sample in the central reservoir 410 has molecules having pI values between 5.0 and 8.0, the higher-pI-selective filtration device 430B may allow molecules having pI values greater than or equal to 7.0 to pass therethrough. Similarly, the lower-pI-selective filtration device 430D may allow molecules having pI values less than or equal to 6.0 to pass therethrough. For purposes of explanation, the higher-pI-selective filtration device 430B will be defined in the second portal 405B and the lower-pI-selective filtration device 430D will be defined in the fourth portal 405D.

According to this example, after step S2 the original sample would be distributed as follows: (a) molecules having pI values greater than or equal to about 8.0 will be in satellite reservoir 420A; (b) molecules having pI values less than or equal to about 5.0 will be in satellite reservoir 420C; (c) molecules having pI values between about 7.0 and about 8.0 will be in satellite reservoir 420B; (d) molecules having pI values between about 5.0 and about 6.0 will be in satellite reservoir 420D; and (e) molecules having pI values between about 6.0 and about 7.0 will be in the central reservoir 410. As a result and as shown in FIG. 5, after the two separation steps S1, S2, five individual samples SAM1, SAM2, SAM3, SAM4, SAM5 can be isolated. Of course, this process can be repeated using additional oppositely charged electrodes 440, 450 and corresponding (and oppositely positioned) satellite reservoirs 420. However, regardless of the number of separation steps employed, after n separations, there will be 2n+1 individual samples.

Each of the previously described apparatus embodiments 100, 200, 300, 400 provides a significant improvement over the prior art as a result of the ability to filter a sample quickly and accurately into a plurality of satellite reservoirs 120, 220, 420 and, if desired, further into a plurality of regional reservoirs 290. Moreover, as a result of being able to combine various types of filtration devices 130, 230, and, if desired, regional filtration devices 235, the filtration can be done both more precisely and more quickly.

Filtration Device Particle Body Examples

Example 1

Preparation of Zirconium Oxide Isoelectric Beads of pI 8.5

A solution of acrylamide monomers in water was prepared as follows. A first solution was made by combining 2.00 mL of water to 171.00 microliters (μL) of a solution containing 4-acrylamidobutyric acid (0.2 molar (M) concentration), 600 μL of 2-morpholinoethylacrylamide (0.2 M concentration), 475 μL of 3-morpholinopropylacrylamide (0.2 M concentration), 190 μL of N,N-dimethylaminoethylacrylamide (0.2 M concentration), and 64 μL of N,N-dimethylaminopropylacrylamide (0.2 M concentration). The first solution of monomers was then added to a second solution containing three milliliters (3.00 mL) of deionized water, 111.00 μL of 1 M acetic acid. To the combined first and second solutions was added 3.33 mL of a third solution of 28.8 grams (g) of acrylamide and 1.2 g of N,N'-methylenebisacrylamide in 100 mL of water.

To the combined first, second, and third solutions, 4.00 milligrams (mg) of ammonium persulfate and 5.00 μL of N,N,N',N'-tetramethylethylenediamine were added and the resulting combination mixed rapidly at a temperature of 4° C.-6° C.

The resulting solution of monomers and polymerization catalysts was mixed together with solid, porous beads of dextran-passivated silica, in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 8.5.

Example 2

Preparation of Zirconium Oxide Isoelectric Beads of pI 5.0

A first solution was prepared by adding 2 ml of water to 310 μL of a solution containing N-acryloylglycine (0.2 M concentration), 229 μL of 4-acrylamidobutyric acid (0.2 M concentration), 235 μL of 2-morpholinoethylacrylamide (0.2 M concentration), 65 μL of 3-morpholinopropylacrylamide (0.2 M concentration), and 190 μL of N,N-dimethylaminopropylacrylamide (0.2 M concentration). The first solution of monomers was added to a second solution containing 3.6 mL of deionized water and 47 μL of 1 M tris-hydroxymethylaminomethane. The combined first and second solutions were then combined with 3.33 mL of a third solution containing 28.8 g of acrylamide and 1.2 g of N,N'-methylenebisacrylamide in 100 mL of water.

The three combined solutions were added with 4 mg of ammonium persulfate and 5 μL of N,N,N',N'-tetramethylethylenediamine and mixed rapidly at a temperature of between 4° C. and 8° C.

The resulting solution of monomers and polymerization catalysts was mixed together with solid, porous beads of dextran-passivated zirconium oxide, sold commercially under the trade name HYPERZ™ by Ciphergen Biosystems, Inc. (Fremont, Calif.), in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 5.0.

Example 3

Preparation of Zirconium Oxide Isoelectric Beads of pI 7.0 (Low Charge)

A first solution of acrylamide monomers was prepared by combining 2 ml of water with: 75 μL of solution of N-acryloylglycine (0.2 M concentration), 475 μL of 4-acrylamidobutyric acid (0.2 M concentration), with 208 μL of 2-morpholinoethylacrylamide (0.2 M concentration), with 106 μL of 3-morpholinopropylacrylamide (0.2 M concentration), 294 μL of N,N-dimethylaminoethylacrylamide (0.2 M concentration), and 177 μL of N,N-dimethylaminopropylacrylamide (0.2 M concentration). The first solution of monomers is added to a second solution of 3.30 mL of deionized water and 13 μL of 1 M acetic acid. The combined solutions are then mixed with 3.33 mL of a third solution that included 28.8 g of acrylamide and 1.2 g of N,N'-methymenebisacrylamide in 100 mL of water. The resulting mixture was then combined with a fourth solution containing 4 mg of ammonium persulfate and 5 μL of N,N,N',N'-tetramethylethylenediamine and mixed rapidly at a temperature between 4° C. and 6° C.

The resulting solution of monomers and polymerization catalysts was mixed together with solid, porous beads of dextran-passivated zirconium oxide, sold commercially under the trade name HYPERZ™ by Ciphergen Biosystems, Inc. (Fremont, Calif.), in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 7.0.

Example 4

Preparation of Zirconium Oxide Isoelectric Beads of pI 7.0 (High Charge)

A first solution of acrylamide monomers in water was prepared by combining 10 mL of water with: 175 mg of solution of N-acryloylglycine, 1.34 g of 4-acrylamidobutyric acid, 690 mg of 2-morpholinoethylacrylamide, 380 mg of 3-morpholinopropylacrylamide, 750 μL of N,N-dimethylaminoethylacrylamide, and 500 mg of N,N-dimethylaminopropylacrylamide. The pI of the solution was adjusted to 7.0 with 1 M acetic acid and then 150 mg of N,N'-methymenebisacrylamide and 1.5 g of acrylamide were added to the solution. The volume of the mixture was then adjusted to 30 mL with deionized water, and with 12 mg of ammonium persulfate and 15 μL of N,N,N',N'-tetramethylethylenediamine were added and the combination mixed rapidly at 4° C.-6° C.

The resulting solution of monomers and polymerization catalysts was mixed together with solid, porous beads of dextran-passivated zirconium oxide, sold commercially under the trade name HYPERZ™ by Ciphergen Biosystems, Inc. (Fremont, Calif.), in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 7.0.

Example 5

Preparation of Silicon Oxide Isoelectric Beads of pI 7.0

A first solution of acrylamide monomers in water was prepared by mixing 2 mL of water with 75 μL of solution of N-acryloylglycine (0.2 M concentration), with 475 μL of 4-acrylamidobutyric acid (0.2 M concentration), 208 μL of 2-morpholinoethylacrylamide (0.2 M concentration), 106 μL of 3-morpholinopropylacrylamide (0.2 M concentration), 294 μL of N,N-dimethylaminoethylacrylamide (0.2 M concentration), 177 μL of N,N-dimethylaminopropylacrylamide (0.2 M concentration). The resulting solution of monomers was combined with a second solution made from 3.3 mL deionized water, 13 μL of 1 M acetic acid; and 3.3 mL of a third solution containing 28.8 g of acrylamide and 1.2 g of N,N-methylenebisacrylamide in 100 mL of water. To the resulting solution was added 4 mg of ammonium persulfate and 5 μL of N,N,N',N'-tetramethylethylenediamine and mixed rapidly at 4° C.-6° C.

The resulting solution of monomers and polymerization catalysts was mixed together with solid, porous beads of dextran-passivated silica in an amount sufficient for the porous volumes of the beads to adsorb substantially of the liquid solution, in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 7.0.

Example 6

Preparation of Isoelectric Beads From Lysine

About 100 g of agarose-zirconia composite beads were mixed with 50 mL of 0.5 M an aqueous sodium hydroxide solution at room temperature. Under shaking, 4 mL of allylbromide (available from Sigma-Aldrich Corp. of St. Louis, Mo.) were added and agitation was continued for about twelve hours (overnight). The allylated beads were then separated by filtration and extensively washed with deionized water, drained, and mixed with 50 mL of deionized water at room temperature and under agitation. Five grams of N-bromosuccinimide (available from Sigma-Aldrich Corp. of St. Louis, Mo.) were added to the suspension, and, after about five minutes, 8.3 g of potassium bromide (Sigma-Aldrich) were also added to the agitated mixture. The pI of the suspension was decreased to a value between 3.7 and 3.9 and maintained in that range of values for sixty minutes. The resulting brominated zirconia beads were then collected by filtration and washed extensively with water and re-suspended in 50 mL deionized water. To this suspension, four grams of L-lysine were added; and the pI of the suspension was immediately adjusted to a value between 9 and 10 and maintained for about two hours at room temperature. The desired zirconia beads supporting covalently attached lysine were washed extensively with water to eliminate any non-reacted material and by-products. The beads were characterized by a titration curve and by the number of charged groups and determined to have an isoelectric point of 8.2.

Although the aforementioned describes embodiments of the invention, the invention is not so restricted. It will be apparent to those skilled in the art that various modifications and variations can be made to the disclosed embodiments of the present invention without departing from the scope or spirit of the invention. Accordingly, these other filter apparatuses and methods of filtering are fully within the scope of the claimed invention. Therefore, it should be understood that the apparatuses and methods described herein are illustrative only and are not limiting upon the scope of the invention, which is indicated by the following claims.

What is claimed is:

1. A filter apparatus comprising:
    (a) a central reservoir configured to contain a sample;
    (b) at least a first, a second, a third, and a fourth satellite reservoir in fluid communication with the central reservoir;
    (c) at least a first, a second, a third, and a fourth portal joining a corresponding one of the at least first, second, third and fourth satellite reservoirs with the central reservoir;
    (d) at least a first, a second, a third, and a fourth filtration device, differing from each other in pI-selectivity,
        wherein the first, second, third, and fourth filtration devices are positioned in the first, second, third, and fourth portals, respectively,
        wherein the first filtration device is either a highest-pI-selective or a lowest-pI-selective filtration device and the second filtration device is the other of the highest-pI-selective or the lowest-pI-selective filtration device, and
        wherein the third filtration is either a higher-pI-selective or a lower-pI-selective filtration device and the fourth filtration device is the other of the higher-pI-selective or the lower-pI-selective filtration device
        wherein the first, second, third and fourth filtration devices comprise a member independently selected from an isoelectric bead bed and a zwitterionic packed particulate material wherein the isoelectric bead bed comprises porous beads coated with a passivating layer, wherein the porous beads are filled with a substance comprising a predetermined isoelectric point; and
    (e) at least a first electrode configured to be in electrical contact with the first satellite reservoir, a second electrode configured to be in electrical contact with the second satellite reservoir, a third electrode configured to be in electrical contact with the third satellite reservoir, and a fourth electrode configured to be in electrical contact with the fourth satellite reservoir,
        wherein the first and the second electrodes are oppositely charged,
        wherein the first and the second satellite reservoirs are oppositely positioned across the central reservoir,
        wherein the third and the fourth electrodes are oppositely charged, and
        wherein the third and the fourth satellite reservoirs are oppositely positioned across the central reservoir,
    wherein in a first separation step, the first and second electrodes are configured to be charged so that molecules move through the highest-pI-selective and lowest-pI-selective filtration devices and into the first and second satellite reservoirs, and
    wherein after the first separation step, the first and second electrodes are configured to be de-charged and the third and fourth electrodes are configured to be charged so that molecules move through the higher-pI-selective and lower-pI-selective filtration devices and into the third and fourth satellite reservoirs, thereby leaving molecules having pI values between the pI-selectivities of the higher-pI-selective and lower-pI-selective filtration devices in the central reservoir.

2. The filter apparatus according to claim 1, further comprising:
    a switching apparatus configured to charge and de-charge the electrodes.

3. The filter apparatus according to claim 1, wherein the filtration devices associated with the satellite reservoirs comprise a zwitterionic packed particulate material.

4. The filter apparatus according to claim 1, wherein the filtration devices associated with the satellite reservoirs further comprises a sequence of barriers, and wherein at least one of the barriers is a zwitterionic packed particulate material.

5. The filter apparatus according to claim 4, wherein the sequence of barriers comprises two or more barriers and at least one of said two or more barriers is a membrane or is particulate matter comprising a selective ligand, and wherein the membrane or particulate matter is positioned between the zwitterionic packed particulate material and the satellite reservoir.

6. The filter apparatus according to claim 4, wherein the particulate material has an irregular or spherical shape.

7. The filter apparatus according to claim 1, wherein the filtration devices associated with the satellite reservoirs further comprise a sequence of barriers, and wherein at least one of the barriers is an isoelectric bead bed.

8. The filter apparatus according to claim 7, wherein the isoelectric bead bed is formed of a polymeric material or a composite material.

9. The filter apparatus according to claim 1, further comprising:
at least one cut-off membrane positioned between at least one electrode and the satellite reservoir associated therewith,
wherein the cut-off membrane is impermeable to molecules greater than 500 Daltons.

10. The filter apparatus according to claim 1, further comprising:
a power source comprising two oppositely charged poles, wherein one of the poles is connected to the first and third electrodes and the other pole is connected to the second and fourth electrodes.

11. The filter apparatus according to claim 1, wherein the electrodes are separated from the central reservoir by a distance of no more than about 1 cm, no more than about 5 cm, no more than about 10 cm, no more than about 15 cm, no more than about 20 cm, no more than about 30 cm, no more than about 35 cm, no more than about 40 cm, no more than about 45 cm, or no more than about 50 cm.

12. The filter apparatus according to claim 1, further comprising:
a sample in the central reservoir, the sample comprising amphoteric molecules.

13. The filter apparatus according to claim 12, wherein the amphoteric molecules comprise proteins.

14. The filter apparatus according to claim 1, wherein the filtration devices have pI-selectivity values that differ from each other in increments selected from the group consisting of about 0.001 pH unit, about 0.01 pH unit, about 0.1 pH unit, and about 1.0 pH unit.

15. The filter apparatus according to claim 1, wherein the central reservoir is configured to rotate or is configured to stir a sample therein.

16. The filter apparatus according to claim 1, wherein the filtration devices further comprise membranes formed of a polyacrylamide gel to which an acrylamido buffer is covalently linked.

17. The filter apparatus according to claim 1, wherein each of the filtration devices comprises an isoelectric bead bed.

18. The filter apparatus according to claim 1, wherein after n separation steps, 2n+1 samples are isolated based on pI value.

19. A filter apparatus comprising:
(a) a central reservoir configured to contain a sample;
(b) at least a first, a second, a third, and a fourth satellite reservoir in fluid communication with the central reservoir;
(c) at least a first, a second, a third, and a fourth portal joining a corresponding one of the at least first, second, third and fourth satellite reservoirs with the central reservoir;
(d) at least a first, a second, a third, and a fourth filtration device,
wherein the first, second, third and fourth filtration devices differ from each other in pI-selectivity,
wherein the first, second, third, and fourth filtration devices are positioned in the first, second, third, and fourth portals, respectively,
wherein the first, second, third and fourth filtration devices comprise an isoelectric bead bed, wherein the isoelectric bead bed comprises porous beads coated with a passivating layer, wherein the porous beads are filled with a substance comprising a predetermined isoelectric point;
(e) a first electrode in electrical contact with the central reservoir,
(f) a primary second electrode in electrical contact with the first satellite reservoir, a secondary second electrode in electrical contact with the second satellite reservoir, a tertiary second electrode in electrical contact with the third satellite reservoir, a quaternary second electrode in electrical contact with the fourth satellite reservoir,
wherein the primary, secondary, tertiary and quaternary second electrodes are configured to have an opposite charge from that of the first electrode;
(g) a switching device configured to charge and de-charge the primary, secondary, tertiary and quaternary second electrodes sequentially.

20. The filter apparatus according to claim 19, wherein the porous beads comprise a mineral oxide.

21. The filter apparatus according to claim 20, wherein the mineral oxide is a member selected from zirconia, silica, titania, alumina, and combinations thereof.

22. The filter apparatus of claim 19, wherein the wherein the first, second, third and fourth filtration devices further comprise a series of barriers, and wherein at least one of the barriers in the sequence of barriers is a membrane or particulate matter comprising a selective ligand, and wherein the membrane or particulate matter is positioned between the isoelectric bead bed and the satellite reservoir.

* * * * *